United States Patent [19]

Threlkel et al.

[11] Patent Number: 5,196,625
[45] Date of Patent: Mar. 23, 1993

[54] DETERGENT GRADE TO $C_{10}$ TO $C_{28}$ OLEFINS, ($C_{10}$ TO $C_{28}$ ALKYL) BENZENES AND ($C_{10}$ TO $C_{28}$ ALKYL) BENZENE SULFONATES AND PROCESS FOR PREPARING SAME USING A PHOSPHITE CONTAINING CATALYST

[75] Inventors: Richard S. Threlkel, Albany; Victor P. Kurkov, San Rafael, both of Calif.

[73] Assignee: Chevron Research & Technology Company, San Francisco, Calif.

[21] Appl. No.: 880,473

[22] Filed: May 6, 1992

Related U.S. Application Data

[63] Continuation of Ser. No. 515,956, Apr. 27, 1990, abandoned.

[51] Int. Cl.$^5$ .................................................. C07C 2/24
[52] U.S. Cl. ......................................... 585/513; 585/514; 585/521; 585/527
[58] Field of Search ................. 585/513, 514, 521, 527

[56] References Cited

U.S. PATENT DOCUMENTS

| | | | |
|---|---|---|---|
| 3,315,009 | 4/1967 | Engelbrecht et al. | 260/683.15 |
| 3,317,628 | 5/1967 | Schuck | 260/683.15 |
| 3,402,217 | 9/1968 | Engelbrecht et al. | 260/683.15 |
| 3,409,703 | 11/1968 | Engelbrecht et al. | 260/683.15 |
| 3,424,815 | 1/1969 | Cannell et al. | 260/683.15 |
| 3,592,870 | 7/1971 | Dunn | 260/683.15 |
| 3,872,026 | 3/1975 | Dunn | 252/429 B |
| 3,910,869 | 10/1975 | Throckmorton | 260/94.3 |
| 4,000,211 | 12/1976 | Smith et al. | 260/683.15 |
| 4,069,273 | 1/1978 | Komoto | 260/683.15 |
| 4,102,817 | 7/1978 | Throckmorton et al. | 252/429 B |
| 4,120,882 | 10/1978 | Wilke et al. | 502/167 |
| 4,187,197 | 2/1980 | Kabanov | 252/431 |
| 4,283,305 | 8/1981 | Chauvin et al. | 252/431 |
| 4,316,851 | 2/1982 | Le Pennec et al. | 260/408 |
| 4,366,087 | 12/1982 | Le Pennec et al. | 252/431 |
| 4,404,415 | 9/1983 | Gaillard | 585/512 |
| 4,677,241 | 6/1987 | Threlkel | 585/526 |
| 4,959,491 | 9/1990 | Threlkel | 562/94 |

OTHER PUBLICATIONS

Du Plessis et al., Chem. Abst. 88, (1978), 7491m.
De Haan et al., Jrnl. of Cat., 44, (1976), pp. 15-24.
Pillai et al., *Chemical Reviews*, 1986, vol. 86, No. 2, pp. 353-399.

*Primary Examiner*—Patrick P. Garvin
*Assistant Examiner*—Brent M. Peebles

[57] ABSTRACT

A dimerization process for producing linear and/or mono-branched $C_{10}$ to $C_{28}$ olefins using dimerization catalysts and new $C_{10}$ to $C_{28}$ olefins mixtures are disclosed. The $C_{10}$ to $C_{28}$ olefin product is especially useful for the production of biodegradable alkylbenzene sulfonates detergents and intermediates therefor.

10 Claims, No Drawings

DETERGENT GRADE TO $C_{10}$ TO $C_{28}$ OLEFINS, ($C_{10}$ TO $C_{28}$ ALKYL) BENZENES AND ($C_{10}$ TO $C_{28}$ ALKYL) BENZENE SULFONATES AND PROCESS FOR PREPARING SAME USING A PHOSPHITE CONTAINING CATALYST

This application is a continuation of application Ser. No. 515,956, filed Apr. 27, 1990 and now abandoned.

BACKGROUND OF THE INVENTION

This invention relates to a process and catalyst for the dimerization of olefins to produce longer chained olefin products. In a further aspect, the invention relates to the production of olefins and alkylbenzenes which are especially useful as intermediates in the production of alkylbenzene sulfonate detergents. The invention also relates to such detergents and their production.

One significant commercial application of longer chained olefins (e.g., $C_{10}$ to $C_{28}$) is as intermediates in the production of alkyl aromatic sulfonate detergents. Since large amounts of such detergents are ultimately released to the environment, the need for biodegradability is well recognized. It is further well recognized that linear and mono-branched alkyl aromatic sulfonates are generally much more readily biodegraded than multi-branched alkyl aromatic sulfonates and, hence, much more desirable as detergents. Thus, the need exists for processes which efficiently produce high yields of $C_{10}$-$C_{28}$ linear and/or mono-branched olefins or olefin mixtures which afford biodegradable alkylbenzene sulfonates.

U.S. Pat. No. 3,315,009, issued Apr. 18, 1967 to Engelbrecht et al., discloses a two-dimerization step process for preparing $C_8$-$C_{16}$ olefins using a heterogeneous cobalt oxide catalyst. Patentee teaches that it is preferred that the dimer feed to the second stage dimerization be substantially linear, but that the presence of branched-chain mono-olefins in the feed to the second stage up to 15% by weight is not deleterious.

U.S. Pat. No. 3,317,628, issued May 2, 1967 to Schuck et al., discloses a two-dimerization step process for preparing higher olefins similar to that described in the aforementioned U.S. Pat. No. 3,315,009, but using a somewhat different heterogeneous cobalt catalyst. Patentee stresses one of the advantages of patentee's process is that the formation of undesired isomers, such as 2-methylpent-2-ene is minimized if not eliminated. Patentee describes 2-methylpent-2-ene as an especially undesirable isomer in hexene fractions for the purpose of patentee's process because it is not separated from n-hexene by commercial methods of distillation and therefore requires special separation procedures or it must remain as an impurity.

U.S. Pat. No. 3,402,217, issued Sep. 17, 1968 to Engelbrecht et al., discloses a two zone polymerization process for preparing higher olefins using a molecular sieve or zeolite catalyst. Patentee teaches that a particularly preferred mono-olefin dimer feed to the second zone polymerization is one which contains no greater than 10% by weight of branched-chain mono-olefins and the remainder straight-chain mono-olefins. Patentee further teaches that generally ordinary fractional distillation is adequate to purify the first dimerization zone product, but that in addition to or in place of fractional distillation, other conventional separation or purification means such as adsorbents, i.e., molecular sieves, solvent extraction, extractive distillation, selective polymerization, isomerization, and the like may be employed to conform the dimer product of the first-stage dimerization to the feed requirements of the second-stage dimerization. Patentee states that it is immaterial to patentee's invention what separation means is used for purifying the product of the first-stage dimerization to meet the feed requirements of the second-stage dimerization, so long as such separation means provides the desired purification.

U.S. Pat. No. 3,409,703, issued Nov. 5, 1968 to Engelbrecht et al., discloses a two-dimerization step process similar to that disclosed in U.S. Pat. No. 3,315,009, but using a modifying agent in the first dimerization.

U.S. Pat. No. 3,424,815, issued Jan. 28, 1969 to Cannell et al., describes the preparation of $\alpha$-olefin oligomers using a catalyst comprising the product of certain nickel chelates with a halide-free organo-aluminum compound such as alkyl aluminum alkoxides. Patentee teaches that the nickel chelating ligand-anion is substituted with electron withdrawing groups, i.e., nitro, halo, cyano or carboalkoxy and that superior results are obtained when the chelating ligands are halogenated organic ligands.

U.S. Pat. No. 3,592,870, issued Jul. 13, 1971 to Dunn, discloses an olefin dimerization process using a catalyst formed from an organoaluminum compound and one of the following nickel complexes: (a) bis($\beta$-mercaptoethylamine)nickel (II) complex; (b) $\alpha$-diketobis($\beta$-mercaptoethylimine)nickel (II) complex; (c) S,S,-disubstituted bis($\beta$-mercaptoethylamine)nickel (II) complex; or (d) S,S,-disubstituted-$\alpha$-diketone bis($\beta$-mercaptoethylimine)nickel (II) complex. Based on the product distribution shown in the examples of this patent, the dimerization of propylene using patentee's catalysts resulted in $C_6$ olefin products containing 63 to 70% branched olefins depending on the particular catalyst used.

U.S. Pat. No. 3,910,869, issued Oct. 7, 1975 to Throckmorton, discloses a process for the polymerization of butadiene and butadiene in mixture with other diolefins to form polymers containing a high proportion of butadiene units in the cis-1,4 configuration. The process involves contacting the monomer under solution polymerization conditions at temperatures ranging from $-10°$ C. to $100°$ C. with a catalyst containing an organoaluminum compound, an organonickel compound and hydrogen fluoride.

U.S. Pat. No. 4,069,273, issued Jan. 17, 1978 to Komoto, describes a process for dimerizing low molecular weight linear $\alpha$-olefins using a complex of bis(1,5-cyclooctadiene)nickel and hexafluoro-2,4-pentanedione as a homogeneous catalyst. Patentee describes his process as producing a highly linear olefin product. U.S. Pat. No. 4,366,087, issued Dec. 28, 1982 to Le Pennec et al., describes a process for oligomerizing olefins using a catalyst containing a hydrocarbyl aluminum halide and a nickel compound having the formula $(R_1COO)(R_2COO)Ni$, wherein $R_1$ is a hydrocarbyl radical having at least 5 carbon atoms and $R_2$ is a haloalkyl radical. As can be seen from the examples in this patent, patentee's process afforded a product containing a large amount of branched olefins. A number of catalyst systems used for the polymerization of olefins are described in *Chemical Review*, 86 (1986), pp. 353-399.

U.S. Pat. No. 4,102,817, issued Jul. 25, 1978 to Throckmorton et al., discloses a process for producing cis-1,4 polybutadiene by contacting butadiene with a catalyst consisting of (1) at least one organoaluminum compound, (2) at least one nickel compound, selected from nickel salts of carboxylic acids, organic complex compounds of nickel and nickel tetracarbonyl, and (3) at least one hydrogen fluoride complex prepared by complexing hydrogen fluoride with a ketone, ester, ether, alcohol, nitrile or water.

U.S. Pat. No. 4,187,197, issued Feb. 5, 1980 to Kabanov et al., discloses a method for dimerizing $C_2$ to $C_4$ olefins using a two component catalyst containing (1) a complex of a nickel salt with a tertiary phosphine or tertiary phosphite and (2) an organoaluminum compound which is a rubber selected from natural and synthetic carbo-chain rubber with a content of 2 to 50 mol % of AlRX units wherein R is an alkyl with at most 8 carbon atoms and X is a halogen, the atomic ratio of Al/Ni being from 1:1 to 100:1.

U.S. Pat. No. 4,404,415, issued Sep. 13, 1983 to Gaillard, discloses a process for producing nonenes and dodecenes from propene. The repeated addition of propene to recycled hexene and nonene reaction products is catalyzed by a catalyst substantially similar to that disclosed in U.S. Pat. No. 4,366,087.

U.S. Pat. No. 4,677,241, issued Jun. 30, 1987 to Threlkel, discloses a process for the oligomerization of a lower olefin having 2 to 8 carbon atoms by contacting the lower olefin with a catalyst containing a transition metal complex selected from complexes of nickel and palladium with a fluoro-organic thiol or sulfide ligand, having a single sulfur atom in a ligating position and wherein the carbon atoms adjacent the carbon to which the sulfur atom is attached has at least one fluoro substituent and with the proviso that the fluoro-organic thiol or sulfide does not contain any other ligating group or atom in a ligating position which will displace the fluoro as a ligand, and an organometallic-reducing agent selected from borohydride and organoaluminum halides and hydroxides.

Although the prior art speaks of highly linear products, seldom are such results obtained except at the cost of low yields or other disadvantages. For example, the two-step processes of the prior art which produce highly linear $C_{10}$-$C_{15}$ olefin products also generally require a highly linear intermediate product, thus effectively wasting significant yields of methyl pentenes which are obtained in the first step reaction product. The prior art systems using heterogeneous catalysts suffer from the usual contact problems incident to such catalysts. Moreover, the heterogeneous catalysts used by the prior art are frequently difficult and expensive to prepare. The use of halide modifying agents also presents a problem since such agents are generally very corrosive and presents equipment problems.

One of the principal uses of $C_{10}$ to $C_{28}$ olefins is as intermediates for detergents and lube oil additives, e.g., sulfonated alkyl benzenes. When used for detergents, the $C_{10}$ to $C_{28}$ olefin product should have a high proportion of linear or mono-branched olefins because detergents produced from predominantly linear olefins are generally more readily biodegraded than those produced from highly branched olefins. Similarly, mono-branched olefins are generally more readily biodegraded than multi-branched olefins and, accordingly, more desirable for detergents. When used as an intermediate for lube oil additives, the $C_{10}$ to $C_{28}$ olefin product should have a high proportion of mono-branched olefins because lube oil additives produced from mainly mono-branched olefins have premium properties such as low pour points or melting points compared to either linear or multi-branched olefins.

Thus, there exists a need for detergent grade $C_{10}$ to $C_{28}$ linear and mono-branched olefins and, accordingly, there exists a need for better processes for preparing detergent grade $C_{10}$ to $C_{28}$ linear and mono-branched olefins.

SUMMARY OF THE INVENTION

In accordance with the present invention, there is provided a process for preparing $C_{10}$ to $C_{28}$ linear and mono-branched olefins comprising contacting a $C_5$ to $C_{14}$ olefin feed with a dimerization catalyst which is selective to the production of linear and mono-branched olefins under dimerization conditions to produce a $C_{10}$ to $C_{28}$ olefin product wherein said dimerization catalyst is selected from the group consisting of:

(1) a mixture comprising:
(a) a nickel (II) compound having the formula NiXY wherein X is an organic carboxy anion RCOO— where R is an aliphatic hydrocarbyl group of at least 4 carbon atoms and Y is a carboxylate or pentane dionylate anion;
(b) a phosphite compound having the formula $P(OR'')_3$ where R'' is a hydrocarbyl group; and
(c) an alkyl aluminum halide;
wherein components (1)(a), (1)(b) and (1)(c) are present in relative amounts such that the P/Ni mole ratio is from about 0.75 to about 1.25 and the Al/Ni mole ratio is from about 5.0 to about 15.0;

(2) a mixture comprising:
(a) a complex of a nickel (O) compound and a phosphite $P(OR'')_3$ where R'' is as defined above; and
(b) an alkyl aluminum halide or aluminum trihalide;
wherein components (2)(a) and (2)(b) are present in relative amounts such that the Al/Ni mole ratio is from about 5.0 to about 7.0; and (3) a mixture comprising:
(a) a mixture of a nickel (O) compound and a phosphite $P(OR'')_3$ where R'' is as defined above; and
(b) an aluminum trihalide;
wherein components (3)(a) and (3)(b) are present in relative amounts such that the Al/Ni mole ratio is from about 5.0 to about 7 0 and the P/Ni mole ratio is from about 1.0 to about 2.0.

The present invention also provides the product produced by the above-described process for making linear and mono-branched $C_{10}$ to $C_{28}$ olefins.

Further provided in accordance with the present invention is a process for preparing ($C_{10}$ to $C_{28}$ linear and mono-branched alkyl) benzene sulfonates comprising the steps of:

A. contacting $C_5$ to $C_{14}$ olefin feed with a dimerization catalyst which is selective to the production of linear and mono-branched olefins under dimerization conditions to produce a $C_{10}$ to $C_{28}$ olefin product wherein said dimerization catalyst is selected from the group consisting of:
(1) a mixture comprising:
(a) a nickel (II) compound having the formula NiXY wherein X is an organic carboxy anion RCOO— where R is an aliphatic hydrocarbyl group of at least 4 carbon atoms and Y is a carboxylate or pentane dionylate anion;
(b) a phosphite compound having the formula $P(OR'')_3$ where R'' is a hydrocarbyl group; and
(c) an alkyl aluminum halide;

wherein components (1)(a), (1)(b) and (1)(c) are present in relative amounts such that the P/Ni mole ratio is from about 0.75 to about 1.25 and the Al/Ni mole ratio is from about 5.0 to about 15.0;

(2) a mixture comprising:
(a) a complex of a nickel (O) compound and a phosphite P(OR") where R" is as defined above; and
(b) an alkylaluminum hallide or an aluminum trihalide;

wherein components (2)(a) and (2)(b) are present in relative amounts such that the Al/Ni mole ratio is from about 5.0 to about 7.0; and (3) a mixture comprising:
(a) a mixture of a nickel (O) compound and a phosphite P(OR")$_3$ where R" is as defined above; and
(b) an aluminum trihalide;

wherein components (3)(a) and (3)(b) are present ni relative amounts such that the Al/Ni mole ratio is from about 5.0 to about 7.0 and the P/Ni mole ratio is from about 1.0 to about 2.0;

B. recovering linear and mono-branched $C_{10}$ to $C_{28}$ olefins from the product of step A;

C. contacting said linear and mono-branched $C_{10}$ to $C_{28}$ olefins with benzene in the presence of an alkylation catalyst under reactive conditions thereby producing a mixture of ($C_{10}$ to $C_{28}$ linear and mono-branched alkyl) benzenes; and D. recovering said ($C_{10}$ to $C_{28}$ linear and mono-branched alkyl)benzenes and contacting said recovered ($C_{10}$ to $C_{28}$ linear and mono-branched alkyl)benzenes with from about 1 to about 1 5 moles, based on sulfur content, of a sulfonating agent per mole of said ($C_{10}$ to $C_{28}$ linear and mono-branched alkyl)benzenes under reactive conditions thereby producing a mixture of ($C_{10}$ to $C_{28}$ linear and mono-branched alkyl)benzene sulfonic acids having the general formula

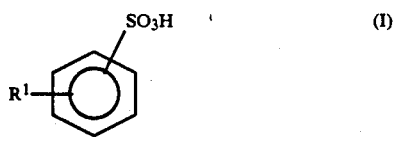

(I)

wherein $R^1$ is linear or mono-branched $C_{10}$ to $C_{28}$ alkyl and neutralizing said ($C_{10}$ to $C_{28}$ linear and mono-branched alkyl)benzene sulfonic acids to yield a mixture of ($C_{10}$ to $C_{28}$ linear and mono-branched alkyl)benzene sulfonate salts.

The present invention also provides the ($C_{10}$ to $C_{28}$ linear and mono-branched alkyl)benzene sulfonate product produced by the above-described process.

Also provided in accordance with another embodiment of the present invention is a process for preparing a mixture of ($C_{10}$ to $C_{28}$ linear and mono-branched alkyl)benzenes comprising the steps of:

A. contacting a $C_5$ to $C_{14}$ olefin feed with a dimerization catalyst which is selective to the production of linear and mono-branched olefins under dimerization conditions to produce a $C_{10}$ to $C_{28}$ olefin product wherein said dimerization catalyst is selected from the group consisting of:

(1) a mixture comprising:
(a) a nickel (II) compound having the formula NiXY wherein X is an organic carboxy anion RCOO— where R is an aliphatic hydrocarbyl group of at least 4 carbon atoms and Y is a carboxylate or pentane dionylate anion;

(b) a phosphite compound having the formula P(OR")$_3$ where R" is a hydrocarbyl group; and
(c) an alkyl aluminum halide;

wherein components (1)(a), (1)(b) and (1)(c) are present in relative amounts such that the P/Ni mole ratio is from about 0.75 to about 1.25 and the Al/Ni mole ratio is from about 5.0 to about 15.0;

(2) a mixture comprising:
(a) a complex of a nickel (O) compound and a phosphite P(OR")$_3$ where R" is as defined above; and
(b) an alkyl aluminum halide or aluminum trihalide;

wherein components (2)(a) and (2)(b) are present in relative amounts such that the Al/Ni mole ratio is from about 5.0 to about 7.0; and (3) a mixture comprising:
(a) a mixture of a nickel (O) compound and a phosphite P(OR")$_3$ where R" is as defined above; and
(b) an aluminum trihalide;

wherein components (3)(a) and (3)(b) are present in relative amounts such that the Al/Ni mole ratio is from about 5.0 to about 7.0 and the P/Ni mole ratio is from about 1.0 to about 2.0;

B. recovering linear and mono-branched $C_{10}$ to $C_{28}$ olefins from the product of step A; and C. contacting said linear and mono-branched $C_{10}$ to $C_{28}$ olefins with benzene in the presence of an alkylation catalyst under reactive conditions thereby producing a mixture of ($C_{10}$ to $C_{28}$ linear and mono-branched alkyl)-benzenes.

Another embodiment of the present invention provides the mixture of ($C_{10}$ to $C_{28}$ linear and mono-branched alkyl)benzenes produced by the above-described process.

DETAILED DESCRIPTION OF PREFERRED EMBODIMENTS

The present invention provides a dimerization process and catalyst which produces excellent yields' typically 90% by weight or higher, of olefin dimers in the $C_{10}$ to $C_{28}$ range, having a very high proportion of linear and mono-branched olefins, typically on the order of 75% by weight or more. Thus, the present process is especially applicable for the production of olefins for use as intermediates used to prepare detergents or lube oil additives. Broadly, the dimerization process of the present invention comprises contacting a $C_5$ to $C_{14}$ olefin feed with the present catalyst under reactive (dimerization) conditions. The olefin feed should contain at least about 70% linear isomers which may be either terminal or internal olefins. Linear α-olefins are not necessary feedstocks for the present invention. Despite the dimerization of completely internal olefins in the present invention, yields of mono-branched and linear olefin dimers typically exceed 75%. This result is surprising since doubly branched olefins are expected from internal olefin dimerization.

By way of illustration, when a $C_6$ olefin feed, such as a mixture of hexenes, is dimerized, the resulting product would be expected to contain a substantial amount of a multi-branched dimer. This is illustrated by the following general reaction scheme:

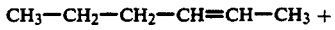

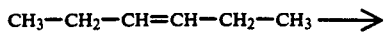

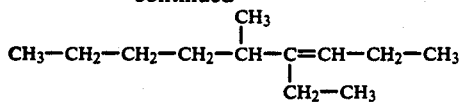

In contrast, when a mixture of hexenes is dimerized in accordance with this invention, high proportions of linear and mono-branched $C_{12}$ olefins are produced. A typical example of a linear $C_{12}$ olefin would be

(where the dotted line represents one possible position for the double bond), and typical mono-branched $C_{12}$ olefins would be

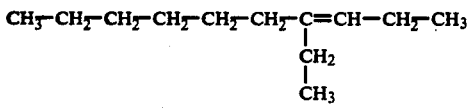

and

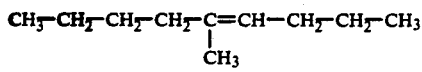

The first step of the present process comprises contacting a $C_5$ to $C_{14}$ olefin feed with a homogeneous dimerization catalyst under reactive conditions. The olefin feed should contain at least about 70% linear olefins and although it may contain other alkenes it should be essentially free of dienes.

Typically, the dimerization is conducted at temperatures in the range of about from about $-10°$ C. to about $100°$ C., preferably from about $10°$ to about $50°$ C. for about ½ to about 8 hours, preferably about 1 to about 5 hours, using an olefin to catalyst mole ratio of about 200 to 20,000, preferably 1,000 to 10,000 moles of olefin per mole of catalyst. The dimerization is generally conducted as a liquid phase reaction using pressures in the range of about 0 to about 3 atmospheres, preferably 1 to 2 atmospheres.

The selection of the catalyst for the dimerization is particularly important. It has been found that the desired yields and selectivity can be obtained by using certain nickel-containing catalysts as the dimerization catalyst, under the conditions indicated above. The dimerization catalysts useful in this invention comprise homogeneous mixtures comprising:

(1) a mixture comprising:
(a) a nickel (II) compound having the formula NiXY wherein X is an organic carboxy anion RCOO— where R is an aliphatic hydrocarbyl group of at least 4 carbon atoms and Y is a carboxylate or pentane dionylate anion;
(b) a phosphite compound having the formula P(OR")$_3$ where R" is a hydrocarbyl group; and
(c) an alkyl aluminum halide;
wherein components (1)(a), (1)(b) and (1)(c) are present in relative amounts such that the P/NI mole ratio is from about 0.75 to about 1.25 and the Al/Ni mole ratio is from about 5.0 to about 15.0;
(2) a mixture comprising:
(a) a complex of a nickel (O) compound and a phosphite P(OR")$_3$ where R" is as defined above; and
(b) an alkyl aluminum halide or aluminum trihalide; wherein components (2)(a) and (2)(b) are present in relative amounts such that the Al/Ni mole ratio is from about 5.0 to about 7.0; or
(3) a mixture comprising:
(a) a mixture of a nickel (O) compound and a phosphite P(OR")$_3$ where R" is as defined above; and
(b) an aluminum trihalide; wherein components (3)(a) and (3)(b) are present in relative amounts such that the Al/Ni mole ratio is from about 5.0 to about 7.0 and the P/Ni mole ratio is from about 1.0 to about 2.0.

Optionally, the catalyst may also contain a small amount of water which has the effect of increasing the rate of the catalytic dimerization. Generally, the amount of water employed will be an amount sufficient to increase the rate of the catalytic dimerization. Typically, the amount of water used will be such that the water/Ni mole ratio will be from about 2:1 to about 5:1.

Examples of the nickel (II) compounds having the formula NiXY include, but are not limited to, bis-(2-ethylhexanoate)nickel; 2-ethylhexanoate nickel trihaloacetate; 2-ethylhexanoate nickel O-chlorobenzoate; and 2-ethylhexanoate nickel acetylacetonate.

Examples of phosphites having the formula P(OR")$_3$ include compounds wherein R" is hydrocarbyl, e g., at each independent occurrence R" may be aryl or $C_1$–$C_8$ alkyl.

Examples of such compounds include, but are not limited to, tri($C_1$–$C_8$ alkyl) phosphites, such as trimethyl phosphite, triethyl phosphite, tripropyl phosphite, tributyl phosphite and the like; triaryl phosphites, such as triphenyl phosphite, tritolyl phosphites; tri(methoxyphenyl)phosphites and the like; and mixed aryl/alkyl phosphites such as dimethyl phenyl phosphite and the like. Trimethyl phosphite is a preferred phosphite because it is relatively inexpensive and readily available.

Examples of alkylaluminum halides useful in the catalysts of the present invention include compounds having the formula R'''$_n$AlZ$_{3-n}$ where R''' is a hydrocarbyl group, e.g., lower ($C_1$–$C_4$) alkyl, Z is halide (preferably Cl) and n = 1 or 2. Alkylaluminum dichlorides, such as ethylaluminum dichloride, are examples of such compounds.

The nickel (O) compounds which are useful in the catalysts of the present invention are in general, nickel (O) compounds which are readily soluble in an organic solvent. Examples of these nickel (O) compounds include, but are not limited to, nickel carbonyl (i.e., Ni(CO)$_4$).

The complexes of nickel (O) compounds and phosphite P(OR")$_3$ compounds useful in this invention typically have the general formula (CO)$_x$NiL$_{4-x}$ where L is the phosphite ligand and x = 1 or 2. Examples of these complexes include, but are not limited to, bis(triarylphosphite)nickel dicarbonyls, and triarylphosphite nickel tricarbonyls.

The aluminum trihalides useful in the practice of this invention include, but are not limited to, AlCl$_3$.

The dimerization catalysts of the present invention can be used in three forms. The first entails the use of a mixture of a nickel (II) salt NiXY, a phosphite P(OR")$_3$ (which acts as a promoting legand) and an alkylaluminum halide reducing agent. Preferably, X and Y are chosen to solubilize the complex in the olefin to be dimerized, although the NiXY salts need not be completely soluble in the reaction medium, especially if the promoting phosphite complexes with NiXY to aid solvation. Particularly suitable nickel salts are the bis-carboxylates such as bis-(2,ethylhexanoate) Ni (II) because these salts are relatively inexpensive and readily available. The phosphite promoting ligand is of the general formula P(OR")$_3$ where R" is an aryl or substituted aryl group. Triphenyl phosphite is a particularly suitable promoting ligand because it is readily available. The alkylaluminum halide is of the general formula R'''$_n$AlZ$_{3-n}$ where R''' is a low molecular weight alkyl, such as ethyl and n=1 or 2. Ethylaluminum dichloride is particularly suitable due to its availability and low cost. The mole ratio of Ni:P:Al can vary and is chosen so that the P/Ni mole ratio is from about 0.75 to about 1.25 and the Al/Ni mole ratio is from about 5.0 to about 15.0. Preferably, the P/Ni mole ratio is about 1.0 and the Al/Ni mole ratio is from about 9.0 to about 13.0. A suitable catalyst can also be prepared by exchanging AlCl$_3$ for some of the ethylaluminum dichloride as long as the Al:Ni mole ratio remains above 9 and the ethylaluminum dichloride:Ni mole ratio remains above 5.

The second form of catalyst entails the use of a mixture of a complex of a nickel (O) compound and a phosphite P(OR")$_3$, and an aluminum trihalide. The complex can be prepared by the addition of the appropriate amount of phosphite to, e.g., Ni (CO)$_4$ solutions in the olefin to be dimerized. The aluminum trihalide is most preferably the chloride or bromide or mixed salts of the two halogens. The mole ratio of Ni:P is most preferably 1:1 to 1:2. The mole ratio of Ni:Al is most preferably 1:5 to 1:7.

The third form of catalyst useful in the present invention entails a mixture which contains a mixture of a nickel (O) compound and a phosphite P(OR")$_3$ compound, and an aluminum trihalide.

The dimerization catalysts of this invention can be prepared by contacting the appropriate components of the catalyst in the olefin to be dimerized. Preferably, the components of the catalyst are not mixed together prior to their addition to the olefin feed, as this may cause decomposition of the catalyst. Typically, then, where the catalyst employed is a mixture of a nickel (II) compound, a phosphite P(OR")$_3$ and an alkyl aluminum halide, the nickel (II) compound and the phosphite may be premixed and added to the olefin feed. The alkyl aluminum halide, however, should not be premixed with the nickel (II) compound and phosphite; rather, it should be added to the olefin feed (which already contains the nickel (II) compound and phosphite compound) at the time it is desired to begin the reaction. Added solvents, such as chlorobenzene may be used and do not detract from catalyst performance. Water may be added up to the mole ratio of 5:1 water to nickel to increase the rate of catalytic olefin dimerization. The catalyst is typically prepared at temperatures in the range of from about −10° C. to about 100° C., preferably from about 25° C. to about 50° C.

Where the dimerization is conducted as a batch process, the catalyst can be conveniently prepared in situ in the reactor. The dimerization can also be conducted as a continuous, semi-batch or multi-step process. The dimerization can be conducted using suitable equipment and process detail such as are conventionally employed in this art. Typically, the oligomerization is conducted as a liquid phase reaction by contacting the olefin feedstock, which can be a single olefin or, as is frequently the case, a mixture of olefins, with the present catalyst at temperatures in the range of from about −10° C. to about 100° C., preferably from about 25° C. to about 50° C., using a feedstock to catalyst mole ratio of about 1000 to 100,000. The dimerization is generally conducted at pressures below 2 atmospheres, and preferably sufficient to maintain a liquid phase system, e.g., at about 0 to about 2 atmospheres.

The present process and catalyst is especially useful for the dimerization of $C_5$ to $C_7$ olefins having a high degree of linearity to produce high yields of $C_{10}$ to $C_{14}$ olefins containing a high proportion of linear and mono-branched isomers. Similarly, the present process is useful for the dimerization of $C_7$ to $C_{14}$ olefins having a high degree of linearity to produce high yields of $C_{14}$ to $C_{28}$ olefins containing a high proportion of mono-branched isomers. The product dimers can be isolated from the reaction product mixture by any suitable procedure, for example, distillation, extraction, and the like. Unreacted feedstock can be recycled back to the initial feedstock.

The ($C_{10}$ to $C_{28}$ linear and mono-branched alkyl)benzenes of this invention can be prepared by contacting the aforedescribed $C_{10}$ to $C_{28}$ olefin product with benzene in the presence of a suitable alkylation catalyst (e.g., hydrogen fluoride, aluminum chloride, and the like) under reactive conditions.

Typically, where hydrogen fluoride is used as the catalyst, the alkylation is conducted at temperatures in the range of about from −20° to 65° C., preferably 0° to 55° C., for about ½ to 4 hours, preferably 1 to 2 hours, using mole ratios in the range of about from 5 to 50, preferably 10 to 20 moles of benzene per mole of olefin and catalyst mole ratios in the range of about from 0.25 to 4, preferably 1 to 1.5 moles of benzene per mole of catalyst (i.e., hydrogen fluoride). Because the presence of water in reactions using hydrogen fluoride is known to present corrosion problem, the alkylation is preferably conducted under anhydrous conditions. The ($C_{10}$ to $C_{28}$ linear and mono-branched alkyl)benzene(s) can be recovered from the reaction product by any suitable procedure, for example, by phase separating the ($C_{10}$ to $C_{28}$ linear and mono-branched alkyl)benzene-rich product from the hydrogen fluoride phase; neutralizing any remaining hydrogen fluoride in the ($C_{10}$ to $C_{28}$ linear and mono-branched alkyl)benzene phase; and removing unreacted benzene by distillation.

In the case where aluminum chloride is used as the catalyst, the reaction is conditioned in the presence of acid at temperatures in the range of about 0° to 75° C., preferably 25° to 50° C. for about from ½ to 4 hours, preferably 1 to 2 hours using about from 5 to 50, preferably 10 to 20 moles of benzene per mole of olefin and about from 2 to 8, preferably 3 to 5 moles of benzene per mole of aluminum chloride catalyst. Typically, the presence of the acid is ensured by simply saturating the benzene reactant with an acid such as hydrogen chloride. The ($C_{10}$ to $C_{28}$ linear and mono-branched alkyl)benzene product can be recovered from the reaction product by any suitable procedure such as, for example, aqueous extraction to remove aluminum chloride followed by neutralization and distillation. The ($C_{10}$ to $C_{28}$ linear and mono-branched alkyl)benzene product can be separated from the reaction product mixture by any suitable procedure. Typically, the catalyst is simply decanted off and any remaining catalyst reaction mixture neutralized. The reaction product can then be purified by distillation to remove unreacted benzene, etc.

Regardless of the catalyst used, the alkylation is typically conducted as a liquid phase reaction and is typically conducted at pressures in the range of about from 1 to 10 atmospheres, preferably 1 to 5 atmospheres.

The ($C_{10}$ to $C_{28}$ linear and mono-branched alkyl)benzene sulfonates of this invention may be prepared by sulfonating the ($C_{10}$ to $C_{28}$ linear and mono-branched alkyl)benzenes described above. The sulfonation can be conducted by contacting the ($C_{10}$ to $C_{28}$ linear and mono-branched alkyl)benzene product of the aforedescribed process with a sulfonating agent, either neat, or optionally in an inert organic solvent or liquid medium, under reaction conditions. The sulfonation can also be conducted in the presence of a moderating agent, such as, for example, dioxane. The modifying agent (e.g., dioxane) complexes with the sulfonating agent, thus moderating the speed or intensity of the reaction.

The sulfonation is typically conducted at temperatures in the range of about from $-40°$ to $100°$ C., preferably $0°$ to $50°$ C. for about from 1 to 20 hours, preferably 1 to 10 hours using pressures of about from $\frac{1}{2}$ to 5 atmospheres, preferably 1 to 2 atmospheres. Typically, about from 1 to 1.5, preferably about from 1.05 to 1.25 moles, based on sulfur, of sulfonating agent are used per mole of ($C_{10}$ to $C_{28}$ linear and mono-branched alkyl)benzene. Under these conditions, only monosulfonation of the phenyl moiety of the alkylbenzene occurs.

Suitable sulfonating agents which can be used include, for example, sulfur trioxide, sulfuric acid, chlorosulfonic acid, and the like. Suitable inert organic solvents which can be used include, for example, methylene chloride, dichloroethane, trichloroethane, tetrachloroethane, and the like. Also, although an organic solvent could be used, it is generally preferable to conduct the sulfonation neat.

Since the product of the sulfonation is an acid, i.e.,

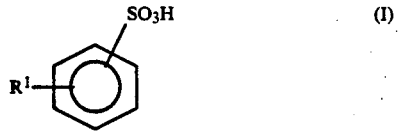

(I)

wherein $R^1$ is $C_{10}$ to $C_{28}$ linear and mono-branched alkyl it is necessary to neutralize the acid to permit its use as a detergent. The sulfonic acid product (I) can be neutralized by simple neutralization with a base to yield the corresponding sulfonate salt. The neutralization can be conveniently conducted in situ with the sulfonation reaction product mixture. [Any excess sulfonating agent can be simply neutralized in situ along with the sulfonic acid product (I).]

Typically, the neutralization is conducted at temperatures in the range of about from $0°$ to $60°$ C. and pressures of about from 1 to 2 atmospheres using about from 1 to 1.1 mole equivalents of base per mole equivalent of sulfonate in the alkylbenzene. Suitable bases which can be used include, for example, alkali metal hydroxides, alkali earth hydroxides, ammonium hydroxides, quaternary ammonium hydroxides, amines, and the like. Typically, the base is added as an aqueous solution. Generally, the selection of the base will be a matter of economics, and for this reason, sodium hydroxide is preferred because it gives good results and is relatively inexpensive. Suitable inert organic solvents which can be used include the same solvents as listed above with respect to the sulfonation. However, typically a solvent is not used because generally it is not necessary and merely adds another separation step to remove the solvent.

The ($C_{10}$ to $C_{28}$ linear and mono-branched alkyl)benzene sulfonate can be recovered from the reaction mixture by any suitable procedure or the reaction mixture can be simply concentrated by evaporating off water added with the base. Any small amounts of unreacted ($C_{10}$ to $C_{28}$ linear and mono-branched alkyl)benzene in the reaction product can be removed by a variety of procedures used in the detergent art, etc., including extraction.

The ($C_{10}$ to $C_{28}$ linear and mono-branched alkyl)benzene sulfonates can be used as detergents in pure form or can be formulated with a variety of builders (sequestering agents) and/or additives such as, for example, are conventionally used in the detergent art.

The present processes and process steps can be conducted as batch, semi-continuous or continuous operations or as a combination of such operations.

It should also be appreciated that where typical or preferred process conditions (e.g., temperatures, times, mole ratios, catalyst ratios, etc.) have been given, that other process conditions could also be used. Optimum reaction conditions (e.g., temperature, reaction time, reactant ratios, catalyst ratios, solvents, etc.) may vary with the particular reactants, catalysts, or solvents used, but can be determined by routine optimization procedures.

A further understanding of the invention can be had from the following nonlimiting examples.

In the following Examples 1–5, all manipulations were carried out under oxygen- and water-free conditions.

EXAMPLE 1

20 Grams of hexenes (containing 90% n-hexenes and 10% methyl-pentenes) was reacted with 27 mgs of nickel bis-(2-ethylhexanoate), 10 mg of trimethyl phosphite, and 101 mgs of ethyl aluminum dichloride in 0.5 g chlorobenzene. After 3 hours of reaction at between 35° C. and 45° C., 50% of the hexenes had reacted. (The percentage of hexenes which react can be increased under different reaction conditions.) The product of these reacted hexenes was 92% dodecenes. 80% of those dodecenes were linear or mono-branched structures.

Analysis of the unreacted starting material showed that very little methyl-pentene enrichment occurred during dimerization. In other words, the hexenes and methyl-pentenes exhibited about equal reactivity with this catalyst. This is important because unreacted hexenes are generally recycled in a continuous process. By using this catalyst, build up of inerts (methyl-pentenes) during recycle is substantially eliminated. Benzene alkylation using these dodecenes (see Example 5) using HF catalyst yielded more than 97% dodecylbenzenes. Less than 1% of lower alkylbenzenes were produced by olefin fragmentation, even when alkylation was carried out at 30° C.

EXAMPLE 2

20 Grams of hexenes (containing 90% n-hexenes and 10% methyl-pentenes) was reacted with 27 mgs of nickel bis(2-ethylhexanoate), 10 mgs of trimethyl phosphite, 80 mgs of ethyl aluminum dichloride, and 11 mgs of aluminum trichloride in 0.5 g of chlorobenzene. After 3 hours of reaction at between 35° and 45° C., 51% of the hexenes were converted to products which contained 92% dodecenes. These dodecenes, as well as the unreacted starting material, was substantially identical to the mixture prepared in Example 1. Substitution of some of the more expensive ethyl aluminum dichloride with less expensive aluminum trichloride is thus demonstrated to give equal or better overall catalyst activity and selectivity.

EXAMPLE 3

8.4 Grams of hexenes (containing 90% n-hexenes and 10% methyl-pentenes) was reacted with 17 mgs of nickel bis(2-ethyl hexanoate), 13 mgs of tributyl phosphite and 64 mgs of ethyl aluminum dichloride in 0.8 g of chlorobenzene. After two hours of reaction at between 35 and 45C, 57% of the hexenes were converted to products which contained 90% dodecenes. 78% of those dodecenes had linear or mono-branched structures. The unreacted starting material consisted of 86% n-hexenes and 14% methyl-pentenes, indicating only a very slight preference by the catalyst for dimerizing the linear olefins. As in Example 1, alkylation of benzene with this dodecene mixture using HF catalyst resulted in a 95+ % yield of dodecylbenzene, with less than 1% loss due to olefin fragmentation.

EXAMPLE 4

6.8 Grams of hexenes (containing 75% n- hexenes and 25% methyl-pentenes) was reacted with 34 mgs of nickel bis(2-ethylhexanoate), 12 mgs of trimethyl phosphite, and 127 mgs of ethyl aluminum dichloride in 0.9 g of chlorobenzene. After 3 hours of reaction at between 35 and 45C, 47% of the hexenes were converted to products which contained 92% dodecenes. 68% of these dodecenes had linear or mono-branched structures. Analysis of the unreacted starting material showed that very little methyl-pentene enrichment had occurred during dimerization.

Benzene alkylation of these dodecenes using HF catalyst resulted in a lower yield (92%) than in the previous Examples. This was due to the higher concentration of methyl-pentenes in the dodecene product.

EXAMPLE 5

26 28 Grams of 1-octene was reacted with 34 mg of nickel bis(2-ethylhexanoate), 12 mg of trimethyl phosphite, and 127 mg of ethyl aluminum dichloride. Analysis of the reaction mixture after 15 minutes of reaction showed that less than 5% 1-olefin remained although less than 20% of the octenes had been converted to dimers. After 5 hours of reaction at between 35° C. and 45° C., 68% of the octenes were converted to oligomers, 90% of which were hexadecenes. 84% of those hexadecenes had linear and mono-branched structures.

EXAMPLE 6

This example demonstrates the utility of the above dodecenes as intermediates for biodegradable alkyl benzene sulfonates and the production of such sulfonates.

44 Grams of the dodecene product isolated from Example 1 was mixed with 283 g of benzene. This mixture was continuously pumped into a reaction solution containing 100 g benzene and 1492 ml of anhydrous hydrogen fluoride in a well-stirred stainless steel autoclave in which the reaction temperature was maintained at 30° C. After all of the olefin/benzene mixture had been injected into the reactor (20 seconds), stirring was continued for another 80 seconds. Phase separation occurred after stirring was stopped and the hydrocarbon layer was recovered and neutralized with caustic and washed with water and dried over sodium sulfate. The acid layer was reused for further alkylations with results substantially identical to this reaction. GC analysis indicated that less than 2% of the dodecene had fragmented. The yield of dodecyl benzene was in excess of 95%. The remaining alkylate consisted of dialkylbenzenes The excess benzene was stripped off and the dodecyl benzene was purified by distillation.

The dodecyl benzene product was sulfonated using standard $SO_3$/air sulfonation reaction conditions. The alkylbenzene was sulfonated in a well-stirred water jacketed reactor equipped with a gas immersion inlet tube. A 10% molar excess of $SO_3$ was added at a rate of about ½ g/minute (for a 100-gram batch of alkylate) as a 6% mixture in dry air through the gas immersion inlet tube. Run temperature was maintained between 35° C. and 50° C. by the 35° C. water jacket. After the $SO_3$ had been added, the sulfonate mixture was cooled, diluted with water and neutralized with sodium hydroxide until the pH was 7.5–8.0.

The biodegradability of this alkyl benzene sulfonate was determined using a hybrid modification of the standard ASTM test method ASTM D 2667 designated biodegradability of alkylbenzene sulfonates, and the Standard OECD Screening Test for primary biodegradability of synthetic surface-active agents. This test measures biodegradability by measuring loss of specific surface activity of the alkylbenzene sulfonate. Thus, the greater the loss of surfactant activity, the greater the biodegradability. The results of this test are shown in Table I below in terms of percent retention of surface activity. Hence, the lower the percent retention, the greater the biodegradability. In addition, a standard (linear alkyl)benzene sulfonate known to be biodegradable and a standard (branched alkyl)benzene sulfonate known to be relatively nonbiodegradable were tested for comparison.

The samples were tested at a concentration of between 2 to 20 ppm in a standard nutrient solution. The solutions were inoculated with a 1% solution of sewage effluent to initiate biodegradation. Surface activity was measured using the ASTM D 2330-82 procedure for methylene blue active substances. The results are shown in Table 1 as a junction of time after inoculation.

TABLE I

|  | Percent Surface Activity Remaining | |
|---|---|---|
|  | Day 7 | Day 10 |
| Standard (Linear Alkyl)benzene Sulfonate | 5 | 3 |
| Standard (Branched Alkyl)benzene Sulfonate | 88 | 65 |
| Dodecyl Benzene Sulfonate from Example 5 | 8 | 4 |

As can be seen from the results recorded in Table I, the aklylbenzene sulfonate derived from the olefin of this invention biodegrades substantially the same as the standard (linear alkyl)benzene sulfonate.

What is claimed is:

1. A process for preparing $C_{10}$ to $C_{28}$ linear and mono-branched olefins comprising contacting a $C_5$ to $C_{14}$ olefin feed with a dimeriztion catalyst which is selective to the production of linear and mono-branched olefins, under dimerization conditions to produce a $C_{10}$ to $C_{28}$ olefin product wherein said dimerization catalyst is selected from the group consisting of:

(1) a mixture comprising:
 (a) a nickel (II) compound having the formula NiXY wherein X is an organic carboxy anion RCOO— where R is an aliphatic hydrocarbyl group of at least 4 carbon atoms and Y is a carboxylate or pentane dionylate anion;
 (b) a phosphite compound having the formula P(OR")$_3$ where R" is a hydrocarbyl group; and
 (c) an alkyl aluminum halide;
 wherein components (1)(a), (1)(b) and (1)(c) are present in relative amounts such that the P/Ni mole ratio is from about 0.75 to about 1.25 and the Al/Ni mole ratio is from about 5.0 to about 15.0;

(2) a mixture comprising:
 (a) a complex to a nickel (O) compound and a phosphite P(OR")$_3$ where R" is as defined above; and
 (b) an alkyl aluminum halide or aluminum trihalide; wherein components (2)(a) and (2)(b) are present in relative amounts such that the Al/Ni mole ratio is from about 5.0 to about 7.0; and (3) a mixture comprising:
 (a) a mixture of a nickel (O) compound and a phosphite P(OR")$_3$ where R" is as defined above; and
 (b) an aluminum trihalide;
 wherein components (3)(a) and (3)(b) are present in relative amounts such that the Al/Ni mole ratio is from about 5.0 to about 7.0 and the P/Ni mole ratio is from about 1.0 to about 2.0.

2. The process of claim 1 wherein the dimerization catalyst is a mixture comprising:
 (a) a nickel (II) compound selected from bis(2-ethylhexanoate) nickel; 2-ethylhexanoate nickel trihaloacetate; 2-ethylhexanoate nickel o-chlorobenzoate; and 2-ethylhexanoate nickel acetylacetonate;
 (b) trialkyl phosphite or triarylphosphite; and
 (c) ethylaluminum dichloride.

3. The process of claim 2 wherein the Al/Ni ratio is from about 9.0 to about 15.0.

4. The process of claim 2 wherein the phosphite is selected from a tri($C_1$-$C_8$ alkyl) phosphite triphenylphosphite, a tritolyl phosphite or a tri(methoxyphenyl)phosphite and dimethyl phenyl phosphite.

5. The process of claim 1 wherein the dimerization catalyst is a mixture comprising:
 (a) a complex of a nickel (O) compound and a phosphite P(OR")$_3$ where R" is a hydrocarbyl group; and
 (b) an alkyl aluminum halide or aluminum trihalide; wherein components (2)(a) and (2)(b) are present in relative amounts such that the Al/Ni mole ratio is from about 5.0 to about 7 0.

6. The process of claim 1 wherein the dimerization catalyst is a mixture comprising:
 (a) a mixture of a nickel (O) compound and a phosphite P(OR")$_3$ where R" is a hydrocarbyl group; and
 (b) an aluminum trihalide;
 wherein components (3)(a) and (3)(b) are present in relative amounts such that the Al Ni mole ratio is from about 5.0 to about 7.0 and the P/Ni mole ratio is from about 1.0 to about 2.0.

7. The process of claim 1 wherein the process is conducted at temperatures in the range of from about $-10°$ C. to about 100° C. and pressures in the range of from about to about 3 atmospheres.

8. The process of claim 1 wherein the $C_5$ to $C_{14}$ olefin feed of the process comprises from about 70 to about by weight of linear $C_5$ to $C_{14}$ olefins.

9. The process of claim 1 further comprising fractionally distilling the reaction product to recover a $C_{10}$ to $C_{28}$ olefin fraction containing linear and mono-branched $C_{10}$ to $C_{28}$ olefins.

10. The process of claim 1 wherein the dimerization catalyst mixtures (1), (2) and (3) further comprise water.

* * * * *